(12) United States Patent
Lamoureux et al.

(10) Patent No.: US 6,554,760 B2
(45) Date of Patent: Apr. 29, 2003

(54) PRE-LOADED NEEDLE ASSEMBLY

(76) Inventors: Gary A. Lamoureux, 373 Old Sherman Hill Rd., Woodbury, CT (US) 06790; Richard A. Terwilliger, 604 Old Field Rd., Southbury, CT (US) 06488

( * ) Notice: Subject to any disclaimer, the term of this patent is extended or adjusted under 35 U.S.C. 154(b) by 0 days.

(21) Appl. No.: 09/983,463

(22) Filed: Oct. 24, 2001

(65) Prior Publication Data

US 2002/0049411 A1 Apr. 25, 2002

Related U.S. Application Data

(60) Provisional application No. 60/242,414, filed on Oct. 25, 2000.

(51) Int. Cl.[7] .................................................. A61N 5/10
(52) U.S. Cl. ........................................................ 600/7
(58) Field of Search .................. 600/1–8; 604/264–266, 604/57, 60

(56) References Cited

U.S. PATENT DOCUMENTS

| 5,460,592 A | * | 10/1995 | Langton et al. ............... 600/7 |
| 6,450,937 B1 | * | 9/2002 | Mercereau et al. ............ 600/7 |
| 6,450,938 B1 | * | 9/2002 | Miller ........................... 600/7 |

* cited by examiner

*Primary Examiner*—Samuel G. Gilbert
(74) *Attorney, Agent, or Firm*—William C. Crutcher

(57) ABSTRACT

For implanting a therapeutic element, this needle assembly includes a cannula having a sharpened distal end, a line of elements in the cannula extending rearward from the distal end. A yieldable positioner including an absorbable plug positions the element more proximate the distal end a predetermined distance from the distal end. The positioner may be in various forms including an end plug, a tab in the cannula. The needle assembly may also be pre-loaded with the line of elements and be sterile and a distortion of the wall of the cannula. A stylet is reciprocable in the cannula and engages the end of the line of elements more remote from the distal end of the cannula.

21 Claims, 2 Drawing Sheets

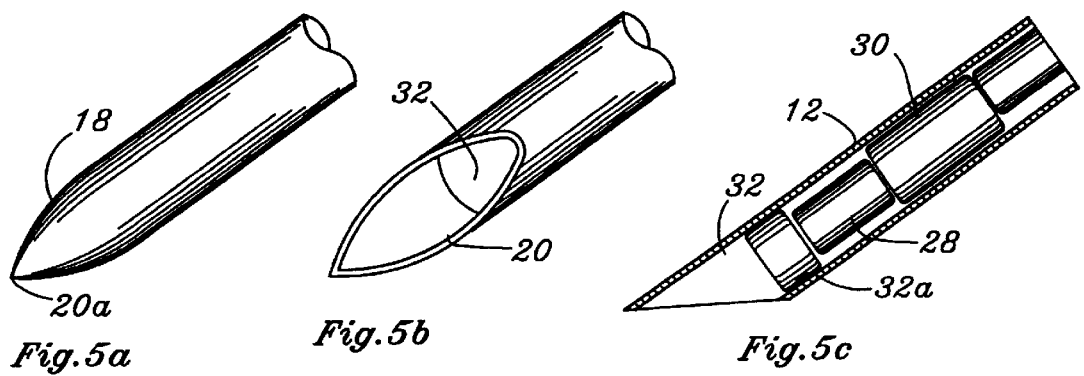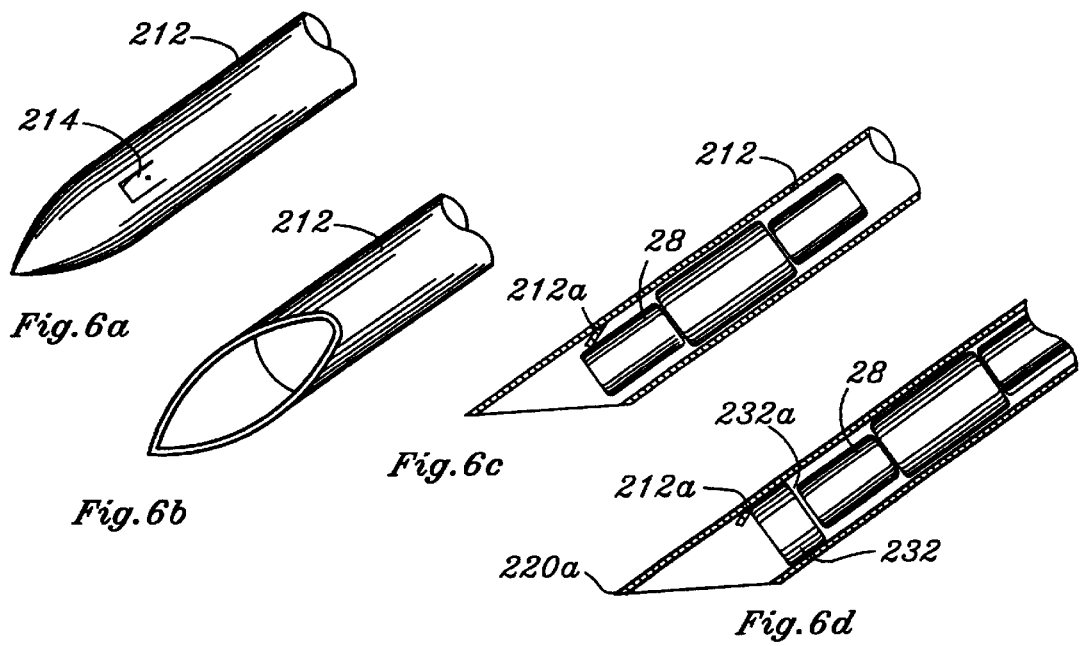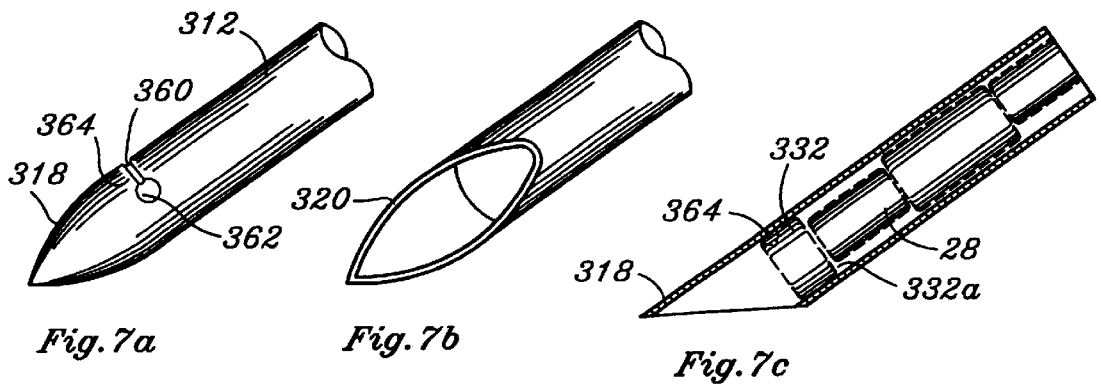

PRE-LOADED NEEDLE ASSEMBLY

This application is related to Provisional patent application Ser. No. 60/242,414 filed Oct. 25, 2000.

FIELD OF THE INVENTION

This invention relates to a needle assembly for implanting therapeutic elements. More specifically, this invention relates to such an assembly which allows the user to load and place radioactive "seeds" in the body for the purpose of treating cancer.

BACKGROUND OF THE INVENTION

The placement of a pattern of radioactive sources in the body to treat cancer by destroying cancer cells with low dose radiation is an accepted and preferred method of treatment as an alternative to general surgery.

These radioactive sources or "seeds" are placed into the body using multiple hollow needles or needle assemblies. The needles act as holders and carriers of such seeds until the needles are inserted into predetermined areas of the body. Once the needles are positioned, the seeds are deployed from each hollow needle by a solid wire stylet to permanently reside in the body as the radioactive dose decays over the treatment time. As many as 25 or more needles are used in each procedure. Typically, a physicist must prepare the needles or cannula and load the seed sources and spacers into each cannula prior to the procedure. Bone wax has been used to close the end of the cannula. The wax is placed into the first 2–5 mm of the distal tip of the cannula to prevent the radioactive "seeds" from dislodging or falling out prior to insertion of the cannula into the body. The doctor then inserts the cannulas into the patient and deploys the seeds into the area to be treated.

Prior art needle assemblies disclose a cannula with a sharpened distal tip and an inner solid wire stylet that is used to push the radioactive seeds into the body. The proximal end of the cannula consists of a plastic or metal hub that allows the loading of the radioactive seeds into the cannula. The proximal end of the stylet is a plastic or metal handle for manipulation of the stylet.

The prior art devices are prepared for use by plugging the end of the cannula with bone wax. The bone wax extends into the first 2–5 mm of the distal tip of the cannula to contain the seeds and to prevent body fluids from entering the cannula before deployment of the seed. The bone-wax-plugged cannula is loaded with radioactive seeds held apart by short non-radioactive spacers that position the seeds in the body to achieve an even distribution of radiation to treat the suspected cancer in vivo.

Prior to insertion, the stylet is axially introduced into the proximal end of the cannula and rests upon the stack of seeds and spacers, which are held in place by the bone wax at the distal tip of the needle. Once the cannula is inserted into the body to the proper position, the stylet is held firm and the cannula is axially moved toward the proximal end of the stylet. This motion deposits the radioactive seeds and spacers into the body in a track or line of seeds as the cannula is pulled back.

There are two principal types of radioactive seeds. "Free" seeds are individual radioactive seeds that are loaded in the cannula with small cylindrical spacers stacked in between the radioactive seeds. The second type is a pre-manufactured "strand" of radioactive seeds that are encapsulated in a biodegradable material that spaces the radioactive seeds apart from one another.

The complications involved in the prior art stem from the use of bone wax or other materials that are used to plug the cannulas prior to the loading of the radioactive seeds.

Bone wax has many drawbacks:

1. Bone wax cannot be applied into the distal end of the cannula in a manner which assures a consistent positioning of the first seed in the cannula. The amount of wax varies needle to needle.
2. Bone wax is sticky and difficult to apply.
3. Bone wax may cause the first few seeds being deployed to stick to the end of the cannula as it is being withdrawn, displacing them from their intended position in the treated tissue (adjacent the prostate, for instance).
4. If the seeds and spacers must be removed after initial loading to change the pattern of seeds and spacers in a given needle, the bone wax prevents the unloading of the seeds in contact with the wax. This prevents the needle from being able to be reused in the procedure.

SUMMARY OF THE INVENTION

The needle assembly of the invention comprises a needle which may be delivered to the user already loaded and sterile. This reduces preparation time as well as personal exposure to the radioactive seeds.

The needle assembly of the invention exactly locates the first seed a repeatable and known distance from the distal end of the cannula in each needle used thus improving the accuracy of placing the radioactive seeds in the body.

The positioning means for the first seed may take one of a variety of forms, all of them yieldable to permit the seed to be pushed past the distal end in the implantation.

The needle assembly of the invention may include a biocompatable end plug which may be made of a variety of materials including absorbable or non-absorbable suture materials either in a braided or monofilament configuration or molded biocompatable polymers. In one embodiment of the invention, the plug may be held in place by a mechanical detail proximal to the distal end of the cannula.

This detail may be formed by parallel slits in the body of the cannula, a "U" shaped cutout in the cannula creating a "tongue" that can be displaced into the interior of the cannula, or small holes that pierce the tubular body of the cannula leaving a web between the holes. In each instance the "web" of needle material created by the hole or slitting process in the tubular body of the cannula allows for a predetermined sizing of the inner diameter of the cannula to hold the end plug or seeds in place prior to deploying them into the body.

In an alternate embodiment of the invention, holding the biocompatable end plug in place inside the cannula at the distal end of the cannula may be accomplished by modifying the diameter of the plug by mechanical distortion means or expanding the diameter of the plug by heating the material until it swells or exposing the plug to solvents.

By enlarging the diameter of the biocompatable end plug, there is created a tight fit between the plug and the cannula body at the distal tip.

The stylet of the inventive needle may be provided in a hollow tubular form. The tube used in the stylet extends through the stylet handle to create an air passageway. This hollow stylet is provided to prevent air pressure from building up inside of the cannula caused by the tight fit of the stylet and the interior diameter of the cannula. This build-up of air pressure may cause premature dislodging of the seed source as the stylet is introduced into the cannula after loading and prior to expulsion of the seeds in the body.

In the case of encapsulated seed sources, the hollow stylet can capture the tail end of the encapsulated strand and prevent the tail end from becoming entrapped between the inner diameter of the cannula and the outer diameter of the stylet during its deployment.

In essence, for implanting a therapeutic element, the invention is a needle assembly comprising a cannula having a sharpened distal end, a line of elements in the cannula extending rearward from the distal end and yeildable means for positioning the element more proximate the distal end a predetermined distance from the distal end. The assembly also includes a stylet reciprocable in the cannula and engaging the end of the line of elements more remote from the distal end of the cannula.

BRIEF DESCRIPTION OF THE DRAWINGS

Further objects and features of the invention will be clear to those skilled in the art from a review of the following specification and drawings, all of which present a non-limiting form of the invention. In the drawings:

FIGS. 5a, 5b and 5c are enlarged fragmentary top, bottom and sectional views respectively of the preferred embodiment.

FIGS. 6a, 6b and 6c are enlarged fragmentary top, bottom and sectional views respectively of a modified form of the invention.

FIG. 6d is similar to FIG. 5c but showing the combination with an end plug, and

FIGS. 7a, 7b and 7c are fragmentary top, bottom and sectional views respectively of a further modified form of the invention.

DESCRIPTION OF THE PREFERRED AND OTHER EMBODIMENTS

Figure 1:
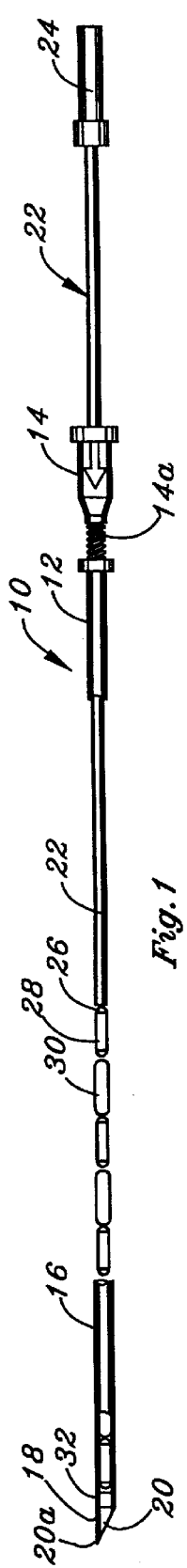
FIG. 1 is a side view with the cannula partly broken away of a preferred needle assembly embodying the invention.

A preferred embodiment of needle assembly of the invention is shown in FIG. 1 and generally designated 10. It comprises a cannula 12 having a hub 14 formed with gripping surfaces 14a. The cannula has a tubular body 16 broken away in FIG. 1 to show its contents and a sharpened distal end 18 beveled off at 20 to provide a point 20a.

Reciprocably disposed in the cannula is the wire stylet 22 having an handle 24 it its proximate end. The distal end of the stylet comprises an engagement surface 26.

Also disposed within the cannula is a line of therapeutic elements, for instance, radioactive seeds 28. The seeds 28 alternate with spacers 30 of cylindrical shape and made of a biocompatable and biodegradable material such as catgut.

An end plug 32 is disposed at the distal end of the cannula. The end plug comprises a rearward cylindrical end surface 32a (FIG. 2) which is positioned at an exact length back from the extreme distal end of the tip 20a of the beveled point 20. This distance is critical and it does not vary from assembly-to-assembly.

The means by which the end plug 32 is positioned in the cannula with its end surface 32a at the pre-determined distance back may be based on one of a variety of structures and techniques. To begin with, the material of the end plug is again biocompatable and biodegradable. It may be formed, for instance, of processed collagen (catgut), Nylon or various other organic substances. A preferred material is polyglactin acid (PGA) available under the trademark POLYGLACTIN 910.

The end plug 32 may be positioned as a friction fit pressed into the distal end of the cannula as a cork in a bottle. Alternatively, it may be treated with a solvent so that it adheres to the inside of the cannula wall. By another technique it may be put in position and the cannula heated to cause the end plug to swell and hold its position. As an additional variation, the cannula may be infinitesimally distorted externally to cause it to "shrink" in the area of the plug and thereby hold the plug in position.

In all embodiments, no matter by what means, the end plug is yieldably held in precise position and may be forced outward as the cannula is drawn backward on the stylet. Thus, the positioning of the end plug 32 in the cannula 12 is yieldable. Before yielding, the plug seals the needle and keeps the seeds from spilling out the needle or body fluids from entering the needle prematurely.

Figure 2:
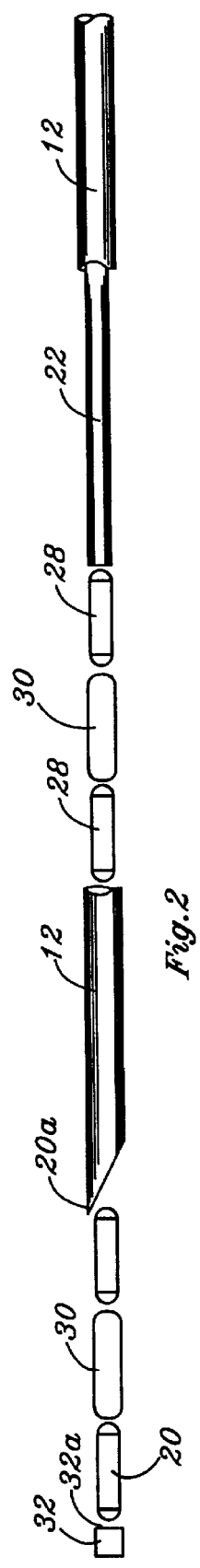
FIG. 2 is a fragmentary enlarged view partly exploded, of the distal end of the assembly.

In more detail, in the operation of the needle assembly shown in FIGS. 1 and 2, as with the other embodiments to follow, the needle assembly is inserted in the tissue of the body to be treated, distal end first. When the insertion is to the desired depth, the stylet 22 is held firmly and the cannula is drawn back toward the handle 24 of the stylet causing the end plug 32 to give way from its initial position and deposit in the tissue the line of seeds and spacers. This operation leaves the seeds in the exact desired position in the body.

It will be understood that the exact positioning of the rear end surface 32a at the pre-established distance back from the tip 20a is a significant advance over the haphazard positioning of the more proximate end of a bone wax material as used in the needle assemblies of the prior art. The arrangement of the present disclosure enables the operator to be assured of the precise positioning of the front end of the first seed 28 and the succeeding spaced seeds as they are inserted.

Figure 3:
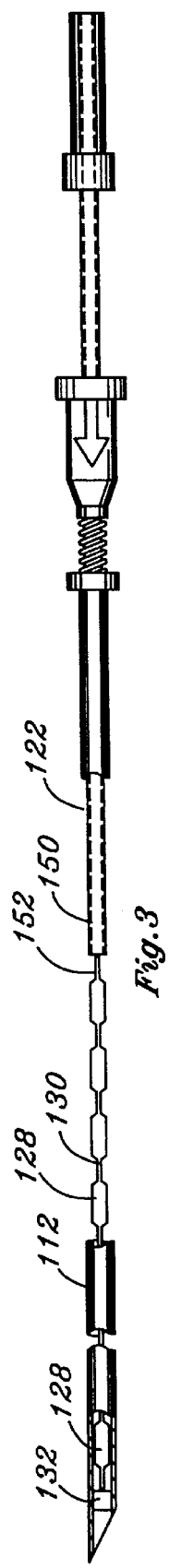
FIG. 3 is a side view with the cannula partly broken away showing use with an encapsulated line of seeds.
Figure 4:
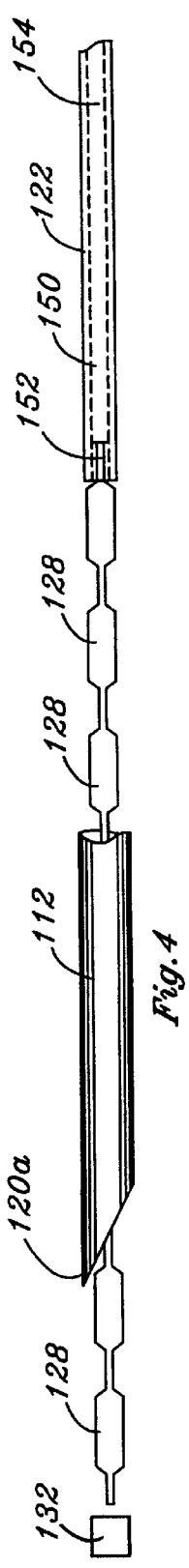
FIG. 4 is a fragmentary enlarged view, partly exploded, of the distal end of the assembly of FIG. 3.

FIGS. 3 and 4 show a similar arrangement of the plug 132—numerals augmented by 100 are used to designate corresponding parts—in the cannula 112, but instead of the line of seeds and spacers 28, 30, there is the encapsulated line of seeds 128 connected by spacing webs 131.

For the encapsulated seeds versions shown in FIGS. 3 and 4, the stylet 122 may be provided with a cylindrical recess 150 to receive the tail 152 on the proximate end of the encapsulated seeds. If desired, the cylinder recess 150 may be extended rearwardly in the form of a vent 154 which extends all the way to the end of the stylet. Such an axial vent of the stylet is also contemplated for the FIGS. 1 and 2 and other embodiments. The purpose of the vent as stated is to prevent a pressure build-up as the stylet is introduced into the cannula. Such pressure can result from the close fitting nature of the stylet in the cannula and can have the effect of a piston in a cylinder pumping inadvertent pressure on the line of seeds and spacers 28, 30 to move them prematurely.

FIGS. 5a, 5b and 5c are enlarged views of the distal end of the cannula in the FIGS. 1, 2 embodiment. FIG. 5a, a sectional view shows the plug 32 in place with the seeds 28 and spacers 30 lined up behind it. As stated, the plug 32 may be a friction fit or may be held in place by a solvent coating to adhesively fix the plug in place, or by heat or by minute distortions of the cannula.

In the modification of FIGS. 6a, 6b and 6c, the first seed 28 is held in place by a tongue 212a which is formed from a U-shaped incision (FIG. 6) 214 wherein the legs "U" are longitudinal of the cannula 212. The cannula wall portion between the legs is bent inward of the cannula so that the distal end of the tongue engages the first seed 28 (FIG. 6c) and yieldably holds it in place. When the cannula is drawn back along the stylet, the pressure on the line of seeds will cause the tongue 212a to yield and permit the first seed 28 in the line of spacers and seeds thereafter to move past the tongue and assume their proper place in the tissue. Thus, in the 6a, 6b and 6c embodiment, the first seed 28 is positioned precisely, but rather than by the rear surface of a end plug, it is by distortion of the cannula itself, namely, the tongue 212a which engages the first seed 28.

In the FIG. 6d variation the end plug 232 is engaged by the tongue 212a and the plug, rather than the seed 28, is yieldably held in position with the rear surface 232a of the plug in the exact pre-determined position in the cannula back from the point 220a.

In the embodiment shown in FIGS. 7a, 7b and 7c, the cannula 312 is formed adjacent the distal end 318 with a pair of spaced openings 360 and 362. A bridge 364 in the cannula wall between the openings 360 and 362 is deflected inward in U-shape (FIG. 7c) to frictionally engage the plug 332 and hold the plug yieldably in place until it is pressed outward by the first seed 28. Here again, the rearward surface 332a is the means for precise positioning of the forward end of the first seed.

Other variations of the invention are contemplated. In every variation the positioning of the first seed 28 is consistently established by the surface against which it abuts. Usually the abutment surface is in the form of the rear surface of a plug, but, as in the FIG. 6c arrangement, the positioning of the lead end of the first seed 28 may be a mechanical yieldable portion of the cannula itself.

Further variations in the invention are possible. Thus, while the invention has been shown but in a few forms, it is not so limited but is of a scope defined by the following claim language which may be broadened by an extension of the right to exclude others from making, using or selling the invention as is appropriate under the doctrine of equivalents.

What is claimed is:

1. For implanting therapeutic elements, a needle assembly comprising a cannula having a wall and a sharpened distal end, a line of elements in the cannula extending rearward from the distal end, yieldable means, including a plug, for positioning an element more proximate the distal end a predetermined distance from the distal end, and a stylet reciprocable in the cannula and having a distal end engaging an end of the line of elements more remote from the distal end of the cannula.

2. A needle assembly as claimed in claim 1 wherein the means for positioning includes an absorbable plug.

3. An assembly as claimed in claim 1 wherein the line of elements is encapsulated in a biodegradable material, the seeds being held in spaced relation by the biodegradable material.

4. An assembly as claimed in claim 1 wherein the line of elements has a rearward tail and the distal end of the stylet is formed with an axial recess receiving the tail.

5. An assembly as claimed in claim 1 wherein the wall of the distal end of the cannula is formed with an irregularity cooperating with said plug to comprise the means for positioning.

6. An assembly as claimed in claim 5 wherein the irregularity is an inward hump in the wall of the cannula between the slits.

7. An assembly as claimed in claim 1 wherein the wall is longitudinally slitted at peripherally spaced location and the wall is deflected inward between two adjacent slits to form an inward tab cooperating with said plug to comprise the means for positioning.

8. An assembly as claimed in claim 7 wherein the inward tab extends inward from the wall of the cannula and has a U-shaped outline.

9. For implanting a therapeutic element, a needle assembly comprising a cannula having a wall and having a sharpened distal end, a generally cylindrical end plug frictionally held in the distal end having a rearward end extending from the distal end a pre-determined distance, a line of elements in the cannula contacting the plug and extending rearward therefrom, and a stylet reciprocable in the cannula and having a distal end engaging an end of the line of elements more remote from the distal end of the cannula.

10. An assembly as claimed in claim 9 wherein the line of elements is encapsulated in a biodegradable material, the seeds being held in spaced relation by the biodegradable material.

11. An assembly as claimed in claim 9 wherein the line of elements has a rearward tail and the distal end of the stylet is formed with an axial recess receiving the tail.

12. An assembly as claimed in claim 9 wherein the wall of the distal end of the cannula is formed with an irregularity to enhance the frictional holding of the plug.

13. An assembly as claimed in claim 12 wherein the irregularity is in the form of a tab extending inward of the wall.

14. An assembly as claimed in claim 12 wherein the wall is formed with peripherally spaced openings and an inward hump is deflected inward between the openings to comprise the irregularity.

15. An assembly as claimed in claim 9 wherein the stylet is formed with an axial vent.

16. An assembly as claimed in claim 9 wherein said end plug seals the distal end of the needle assembly and wherein the needle assembly is pre-loaded with said line of elements and is sterile.

17. A method of making a needle assembly for implanting radiation seeds, comprising the steps of:

a. providing a cannula having a sharpened distal end and a generally cylindrical plug, b. forcing the plug into the sharpened distal end of the cannula to frictionally reside there.

18. A method of making a needle assembly for implanting therapeutic elements, comprising the steps of:

a. providing a cannula having a wall and having a sharpened distal end and providing a generally cylindrical plug, b. placing the plug into the sharpened distal end of the cannula to reside there, and c. modifying the diameter of the plug to enhance its frictional engagement with the wall of the cannula.

19. A method as claimed in claim 18 wherein the diameter is modified by heating.

20. A method as claimed in claim 18 wherein the diameter of the plug is modified by treating the plug with a solvent.

21. A method as claimed in claim 18 wherein the diameter of the plug is modified by mechanical distortion.

* * * * *

UNITED STATES PATENT AND TRADEMARK OFFICE
CERTIFICATE OF CORRECTION

PATENT NO.   : 6,554,760 B2                                        Page 1 of 1
DATED        : April 29, 2003
INVENTOR(S)  : Gary A. Lamoureux and Richard A. Terwilliger It is certified that error appears in the above-identified patent and that said Letters Patent is hereby corrected as shown below:

Column 5,
Line 46, insert -- frictionally held -- following "including a".

Signed and Sealed this

Twenty-fifth Day of November, 2003

JAMES E. ROGAN
*Director of the United States Patent and Trademark Office*

US006554760C1

(12) INTER PARTES REEXAMINATION CERTIFICATE (1006th)
United States Patent
Lamoureux et al.

(10) Number: US 6,554,760 C1
(45) Certificate Issued: Dec. 8, 2014

(54) PRE-LOADED NEEDLE ASSEMBLY

(75) Inventors: Gary A. Lamoureux, Woodbury, CT (US); Richard A. Terwilliger, Southbury, CT (US)

(73) Assignees: Worldwide Medical Technologies, L.L.C.; World Wide Medical of Florida, L.L.C.

Reexamination Request:
No. 95/001,988, Jun. 8, 2012

Reexamination Certificate for:
Patent No.:    6,554,760
Issued:        Apr. 29, 2003
Appl. No.:     09/983,463
Filed:         Oct. 24, 2001

Certificate of Correction issued Nov. 25, 2003

Related U.S. Application Data

(60) Provisional application No. 60/242,414, filed on Oct. 25, 2000.

(51) Int. Cl.
    *A61M 36/00*        (2006.01)

(52) U.S. Cl.
     USPC .................................................. 600/7
(58) Field of Classification Search
     None
     See application file for complete search history.

(56) References Cited

To view the complete listing of prior art documents cited during the proceeding for Reexamination Control Number 95/001,988, please refer to the USPTO's public Patent Application Information Retrieval (PAIR) system under the Display References tab.

*Primary Examiner* — Beverly M Flanagan

(57) ABSTRACT

For implanting a therapeutic element, this needle assembly includes a cannula having a sharpened distal end, a line of elements in the cannula extending rearward from the distal end. A yieldable positioner including an absorbable plug positions the element more proximate the distal end a predetermined distance from the distal end. The positioner may be in various forms including an end plug, a tab in the cannula. The needle assembly may also be pre-loaded with the line of elements and be sterile and a distortion of the wall of the cannula. A stylet is reciprocable in the cannula and engages the end of the line of elements more remote from the distal end of the cannula.

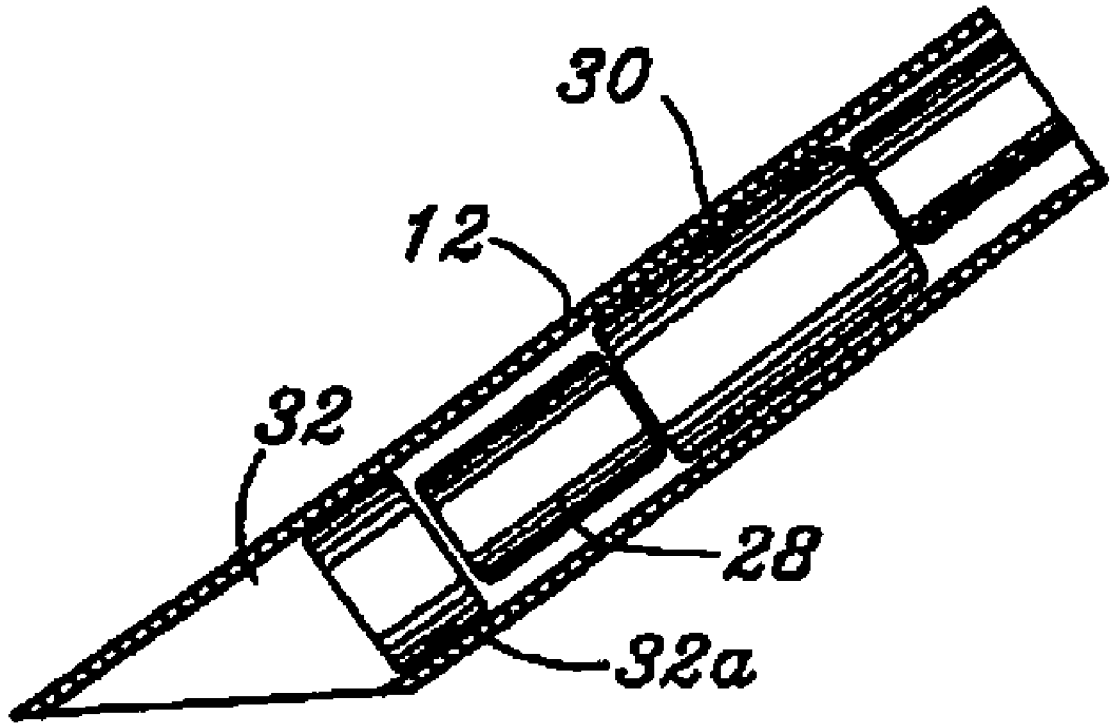

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 19 and 20 is confirmed.

Claims 1-18 and 21 are cancelled.

\* \* \* \* \*